(12) United States Patent
Pierson et al.

(10) Patent No.: US 8,425,480 B2
(45) Date of Patent: Apr. 23, 2013

(54) LOCATION OF FATTY ACID ESTERS ON TAMPONS AND TOXIN INHIBITING EFFICACY

(75) Inventors: Linda M. Pierson, Flemington, NJ (US); Susan K. Brown-Skrobot, Hillsborough, NJ (US); Ching-Yun M. Yang, Princeton Junction, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 719 days.

(21) Appl. No.: 12/622,482

(22) Filed: Nov. 20, 2009

(65) Prior Publication Data

US 2010/0136089 A1 Jun. 3, 2010

Related U.S. Application Data

(60) Provisional application No. 61/116,929, filed on Nov. 21, 2008.

(51) Int. Cl.
*A61F 13/15* (2006.01)
*A61F 13/20* (2006.01)

(52) U.S. Cl.
USPC ..................... 604/385.01; 604/367

(58) Field of Classification Search .................. 604/359, 604/360, 367, 385.17, 385.18
See application file for complete search history.

(56) References Cited

U.S. PATENT DOCUMENTS

| | | | |
|---|---|---|---|
| 3,796,219 A | 3/1974 | Hanke | |
| 4,294,253 A | 10/1981 | Friese | |
| 4,438,167 A | 3/1984 | Schwarz | |
| 4,582,717 A | 4/1986 | von Bittera et al. | |
| 4,642,108 A | 2/1987 | Sustmann | |
| 5,295,984 A | 3/1994 | Contente et al. | |
| 5,389,374 A | 2/1995 | Brown-Skrobot | |
| 5,466,685 A | 11/1995 | Brown-Skrobot et al. | |
| 5,547,985 A | 8/1996 | Brown-Skrobot et al. | |
| 5,633,245 A | 5/1997 | Brown-Skrobot et al. | |
| 5,641,503 A | 6/1997 | Brown-Skrobot | |
| 5,679,369 A | 10/1997 | Brown-Skrobot | |
| 5,705,182 A | 1/1998 | Brown-Skrobot | |
| 5,753,252 A | 5/1998 | Brown-Skrobot | |
| 5,832,576 A | 11/1998 | Leutwyler et al. | |
| 6,310,269 B1 | 10/2001 | Friese et al. | |
| 6,316,019 B1 | 11/2001 | Yang | |
| 6,537,414 B1 | 3/2003 | Schoelling | |
| 6,570,055 B2 | 5/2003 | Yang et al. | |
| 6,748,634 B2 | 6/2004 | Nguyen et al. | |
| 2002/0143305 A1 | 10/2002 | Yang et al. | |
| 2002/0151859 A1 | 10/2002 | Schoelling | |
| 2004/0067214 A1* | 4/2004 | Krautkramer et al. | ....... 424/76.3 |
| 2009/0227975 A1* | 9/2009 | Dougherty et al. | ........... 604/367 |

OTHER PUBLICATIONS

European Pharmacopoeia, Fifth Edition, vol. 2, Published in accordance with the Convention on the Elaboration of a European Pharmacopoeia (European Treaty Series No. 50), 2004, ISBN: 92-871-5281-0, "Viscose Wadding, Absorbent" Jan. 2005:0217, p. 2681-2682.

Reiser et al., "Production of Toxic Shock Syndrome Toxin 1 by *Staphylococcus aureus* Restricted to Endogenous Air in Tampons", *Journal of Clinical Microbiology*, vol. 25, No. 8, Aug. 1987, p. 1450-1452.

\* cited by examiner

*Primary Examiner* — Michelle M Kidwell

(57) ABSTRACT

The application of active ingredients, exemplified by GML, to absorbent fibers, such as rayon fibers, used in tampon manufacture at very low levels has been found to maintain efficacy in the inhibition of the production of toxic shock syndrome toxin one (TSST-1) produced by *S. aureus* without overtly killing the microorganism to achieve the desired reduction while avoiding undesired test results that suggest the presence of "impurities" in some jurisdictions.

5 Claims, No Drawings

LOCATION OF FATTY ACID ESTERS ON TAMPONS AND TOXIN INHIBITING EFFICACY

This application claims the benefit of U.S. provisional application No. 61/116,929 filed on Nov. 21, 2008, the complete disclosure of which is hereby incorporated herein by reference for all purposes.

The present invention is related to the commonly assigned copending patent application entitled "Coating Composition Coating Compositions and Coated Substrates for Articles of Manufacture used in Contact with Human Body Surfaces," U.S. Ser. No. 61/116,785, filed on Nov. 21, 2008, and U.S. Ser. No. 61/116,826, (entitled "Chiller Box," filed on Nov. 21, 2008.

BACKGROUND OF THE INVENTION

The invention relates to absorbent products including tampons, sanitary napkins, wound dressings and the like which absorb body fluids like menstrual fluid, blood, and wound exudates. The specific invention involves the determination of the preferred location of fatty acid esters such as glycerol monolaurate ("GML") on the cover of the product and/or 10% of the fiber to result in a product which delivers a reduction in toxin production by microorganisms utilizing significantly lower concentrations of additive than that described in U.S. Pat. No. 5,641,503.

Direct addition of GML to fibers results in undesired increases in measurable solvent-extractable compositions and foaming.

The published prior art reports the potential use of a surfactant, GML, as a fiber finish for tampons in multiple patents including U.S. Pat. Nos. 57,532,522, 5,679,369, 5,705,182, 5,641,503, and 5,389,374. All patents describe the addition of GML to tampons to reduce the production of toxins from Staphylococcus aureus ("*S. aureus*") as well as other bacteria including *Strept*. spp. The uniqueness of GML as an additive to tampons is that GML solubility in water is much less than 10% and thus remains coated on the tampon materials to provide a continued benefit. Thus, GML can be retained on the fiber as compared with other known fiber finishes which are water soluble and therefore, any preferential location of the typical fiber finishes to the tampon would result in the finish immediately washing away because of the total solubility of the surfactant finishes. Further, the fact that GML is able to reduce the TSST-1 production without significantly affecting the viability of *S. aureus* would suggest that GML addition to the tampon would not disrupt the normal flora of the vaginal vault.

Utilization of GML on fibers and/or covers in the aforementioned patents describe by example a minimum of 0.1% GML being added to the tampons. The patents describe simple pipeting onto the surface of the tampons without describing the potential benefits of uniformity, minimizing add-on and location of GML to allow for the beneficial effect of GML on *S. aureus* toxin production while allowing the product to have reduced extractables and foaming. The patents do not describe how to add GML in an effective concentration onto the absorbent structure (either absorbent core or cover) while providing desirable uniformity and a level of efficacy while still allowing for the beneficial effects of GML against toxin production by bacteria.

Addition of GML to the cover only and/or addition to only 10% of the fiber results in significant reduction in TSST-1 production by *S. aureus*. TSST-1 has been reported as the toxin responsible for Toxic Shock Syndrome which is a serious condition associated with tampon use.

SUMMARY OF INVENTION

The present invention relates to inhibiting the production of toxic shock syndrome toxin one (TSST-1) produced by *S. aureus* without overtly killing the microorganism to achieve the desired reduction without incorporating excess ether and water soluble substances and excess foaming. In order to achieve this invention, the active ingredient for testing was determined to be GML. At the concentrations described in the prior art, the GML provides the TSST-1 reduction capability but the tampons produce elevated extractable levels and foaming that may be undesirable. Therefore, a discovery was made that by placing the GML on only a portion of the fiber (e.g. 10%) used to produce tampons provides an absorbent structure with acceptable extractable and foaming properties while maintaining a level of reduction in TSST-1 without significantly affecting *S. aureus*. Another discovery provides for the preferential location of GML on the plastic and/or nonwoven cover of the tampon while not placing the GML on the fiber results in again a significant reduction in TSST-1 concentration without adversely affecting the *S. aureus* concentration.

DETAILED DESCRIPTION OF THE PREFERRED EMBODIMENT

The present invention describes the application of active ingredients, exemplified by GML, to absorbent fibers, such as rayon fibers, used in tampon manufacture. It has been known that the addition of GML helps to inhibit the production of toxic shock syndrome toxin one (TSST-1) produced by *S. aureus* without overtly killing the microorganism to achieve the desired reduction. However, it is only with the attempt to commercialize tampon products with GML that issues with respect to purity testing in some jurisdictions have arisen. GML and similar active ingredients have surface active properties, and thus can raise extractable levels and foaming levels. This may result in these beneficial compositions being curiously labeled as an "impurity". Indeed at the concentrations described in the prior art, the tampons comprising GML produced levels of extractables and/or foaming that exceeded government established levels in some jurisdictions.

Therefore, applying the GML on only a portion of the fiber (e.g.10 wt-% of the fibers used in the tampon) of the tampon, extractable and foaming levels were maintained at acceptable levels and provided a level of reduction in TSST-1 without significantly affecting *S. aureus*. Alternatively, locating the GML on the plastic and/or nonwoven cover of the tampon while not placing the GML on the fiber results in again a significant reduction in TSST-1 concentration without adversely affecting the *S. aureus* concentration. Further, we have discovered that a combination of these approaches can provide a tampon that has low levels of a component that may be perceived to be an impurity and yet has a sufficient amount of this component to significantly inhibit the ability of *S. aureus* to produce TSST-1. These approaches can provide a tampon that has a sufficiently small amount of GML, about 0.02 wt-% or less on the absorbent fibers, to effectively inhibit TSST-1 production and maintain desired "purity" levels according to Foaming, Ether Soluble Substances, and Water Soluble Substances testing.

We have discovered that effective toxin-reducing amounts of fatty acid esters can be incorporated into tampons in a unique way to provide reduced Foaming, Ether Soluble Substances, and Water Soluble Substances (as described below). We have found that providing less than 0.1 wt-% of the fatty acid esters on the fibrous absorbent structure, preferably less than about 0.08 wt-%, more preferably less than about 0.05 wt-%, even more preferably less than about 0.03 wt-% and most preferably, less than about 0.02 wt-% of the fatty acid esters on the fibrous absorbent structure can result in an absorbent structure that passes the Foaming Test, contains less than 0.3% ether soluble substances according to the Ether Soluble Substances Test, and contains less than 0.7% water soluble substances according to the Water Soluble Substances Test.

We have found that it is difficult to control the application of very low levels of GML to fibers. Therefore, we have found that higher levels of GML can be applied to fibers in a controlled manner, and then these GML-treated fibers can be blended with other fibers to provide the low add-on levels desired in this invention.

We have found that applying a coating of active ingredient, such as GML, onto multilimbed fibers provides effective inhibition of TSST-1 production with low levels of extractables and foaming. While not wishing to be limited by this theory, we believe that the added surface area of the multilimbed fibers, in comparison with substantially cylindrical standard rayon fibers, provides increased surface area for application of GML to provide significant TSST-1 inhibition, even at lower total GML concentration than is taught in the prior art. This permits effective inhibition of toxin production without raising extractables and foaming to unacceptable levels. Thus, the GML treated tampons provide effective toxin inhibition and meet governmental purity standards. This significant improvement permits one to provide health-enhancing tampons without compromising perceptions of product purity and safety.

We have also found that a cover has disposed thereon up to about 5 wt-% of the active ingredient, more preferably between about 0.5 and about 4 wt-%, and most preferably between about 1 and about 3 wt-% of the active ingredient, alone or in conjunction with the active ingredient-treated fibrous absorbent structure provides effective toxin-reducing properties in the articles. This may be provided as described in U.S. Ser. No. 61/116,785, entitled "Coating Composition Coating Compositions and Coated Substrates for Articles of Manufacture used in Contact with Human Body Surfaces," and U.S. Ser. No. 61/116,826, entitled "Chiller Box," both filed on Nov. 21, 2008, the contents of each being hereby incorporated by reference.

The active ingredient can be applied to the cover material through conventional methods, such as spray, roller coating, kiss coating, and slot coating for low viscosity fluid can be applied. Kiss coating and slot coating are preferred for their simplicity and uniformity.

We have found that the active ingredient, e.g., GML, may dissolve into the diluent below, its melting temperature of 58-60° C. It is preferred to heat the formulation to 60° C. or above to insure the formulation stability and low viscosity. For a kiss coater, the formulation add-on and uniformity is controlled by the roller speed vs. line speed. For slot coating, the formulation add-on is determined by slot opening, pump speed, vs. line speed.

GML is very compatible with the diluents; indeed the addition of GML sometimes can make the formulation even more stable than the vehicles without GML. The formulation solidification temperature depends on % GML in the formulation, and often, the best crystallization temperature for the formulation is slightly above the room temperature. It is preferred that the formulation be in liquid form during the coating process for the ease of equipment set-up and to turn into solid after process for the best formulation retention on film and nonwoven covers. It is challenging for the formulation of a high GML add-on. However, we have found that 50% GML/35% PPG/15% SPAN® 80 formulation is in the preferred phase transition zone. We have also seen that water penetration time through cover is very fast, even at high content of hydrophobic GML. It is faster than the film cover coated with hydrophilic PEG, PPG, and TWEEN® 20, alone.

With these coating formulations, we have found that the GML formulation can be uniformly located on one side (coating side) of apertured film material in the form of small depositions, such as micro-droplets. On a nonwoven fabric cover, the GML formulation can be relatively evenly distributed, overall. When looked at microscopically, most of the formulation is located in the small pores around thermal embossed areas. Thus, a most preferred formulation matrix is coated on a nonwoven material. This allows the nonwoven to best entrap and retain the formulation and allows the low formulation areas on cover to be bonded to the sliver for the best cover stability on tampon.

In the examples that follow, the invention will be described in detail in connection with a catamenial tampon comprising an absorbent material, a liquid-pervious covering fabric, and an amount of a mixture of glycerol monolaurate and glycerol dilaurate which is effective to inhibit the production of toxic shock syndrome toxin-1 by *S. aureus* bacteria when said bacteria are brought into contact with the tampon. It will be understood that the principles of the invention apply as well to other absorbent products such as wound dressings, disposable diapers, sanitary napkins and other kinds of tampons, such as those intended for medical, surgical, dental and/or nasal use.

General Procedure for Preparing Tampons of the Invention

A mixture of glycerol monolaurate, glycerol dilaurate and very small amount of glycerol trilaurate, commercially available under the tradename "Monomuls 90 L-12", was obtained from Cognis Corporation, Ambler, Pa., U.S.A. This mixture, which is referred to as GML was analyzed and found to contain >90 percent by weight of glycerol monomoluate while glycerol dilaurate and trilaurate are the remaining 10%. It is know that GML has some limited antimicrobial properties and is non toxic to humans.

GALAXY™ fibers (trilobal viscose rayon fibers, available from Kelheim GmbH) were treated with a 0.2 wt-% GML finish by the following method:

Prepare in-situ sodium laurate solution at a content equivalent to 0.2% by weight of GML via addition of sodium hydroxide and lauric acid and heat it to ~80 C for about 30 minutes.

Add GML to prepare for 5% stock solution

Add the stock solution into rayon and Galaxy finish bath at the rate to achieve target GML add-on. Control bath pH at about 4.

Spray the finish from finish bath on rayon and Galaxy mat.

Send the fiber mat to a set of pressure roll to achieve about 100% moisture add-on.

Dry the fiber in an oven.

These fibers were then blended with untreated standard rayon fibers in the ratios shown in Table 1, the fiber blends were subsequently formed into tampons in accordance with the general teaching of Friese et al., U.S. Pat. No. 6,310,269; Leutwyler et al., U.S. Pat. No. 5,832,576; PPC708; and Schoelling US Pat. App. No. 2002/0151859 employing the apertured film cover, generally as disclosed in U.S. Pat. No. 6,537,414; the disclosures of which are herein incorporated by reference.

The cover was removed, and the resulting fibrous absorbent structure was tested to determine various levels of Foaming, Ether Soluble Substances, and Water Soluble Substances.

Test Methods
Foaming Test

Place 15.0 g of the tampon fibers in a suitable vessel, add 150 ml of water (de-ionized), close vessel and allow to macerate for 2 hours. Decant the solution; squeeze the residual liquid carefully from the sample with a glass rod and mix. Take 10 ml of the solution and introduce into a 25 ml graduated ground-glass-stoppered cylinder with an external diameter of 20 mm and a wall thickness of not greater than 1.5 mm previously rinsed three times with sulfuric acid and then with water (de-ionized). Shake vigorously 30 times in ten seconds, allow to stand for one minute, and repeat the shaking. After five minutes, inspect any foam present. This is reported as "Pass" if the foam does not cover the entire surface of the liquid or "Fail" in the Foaming Test if the foam does cover the entire surface of the liquid.

Ether Soluble Substances Test

Place 5.00 g of the tampon fibers in an extraction apparatus and extract with ether at a rate of at least four extractions per hour for four hours. Evaporate the ether extract and dry the residue to constant mass at 100° C. to 105° C.

Water Soluble Substances Test

Boil 5.00 g of the tampon fibers in 500 ml of water (de-ionized) for 30 minutes, stirring frequently. Replace water lost by evaporation. Decant the liquid; squeeze the residual liquid carefully from the sample with a glass rod and mix. Filter the liquid while hot. Evaporate 400 ml of the filtrate (corresponding to 4/5 of the mass of the sample taken) and dry the residue to constant mass at 100° C. to 105° C.

Tampon Sac Method

This test was reported by Reiser et al. in the Journal of Clinical Microbiology, Vol. 25, August 1987, pp. 1450-1452, the disclosure of which is hereby incorporated by reference. The tampon sac method was utilized as described by Reiser et al., 1987 but utilizing *S. aureus* strain Mn 8 producing TSST-1 of Dr. Patrick Schlievert of the University of Minnesota, Minneapolis, Minn. for evaluation of the effect of GML additive to tampons. The inoculum was prepared by transferring *S. aureus* Mn8 into a nutrient medium and incubating the culture for 18-24hrs at 37° C. prior to use.

100 milliliters of brain heart infusion (BHI) agar (also obtained from Difco Laboratories in Detroit, Mich., U.S.A.) were put into each of ten 3.8 cm×20 cm culture tubes. Cellulose sacs were made and sterilized in the manner reported by Reiser et al. The sterile cellulose sacs were inoculated with the aforementioned *S. aureus* suspension in an amount sufficient to provide at the beginning of the test a concentration therein of $1 \times 10^7$ CFU/ml *S. aureus* bacteria.

The dangling portion of the withdrawal string was cut from the tampon prior to testing. Each GML treated tampon (sample A, B, and C) to be tested was inserted into a sterile cellulose sac containing the *S. aureus* bacteria and each sac was then inserted into a culture tube containing the BHI agar. One control tampon without GML was utilized in triplicate samples were tested and utilized to compare to the treated tampon to determine the percent reduction.

The concentrations of toxic shock syndrome toxin-1 as determined utilizing ELISA after incubation of *S. aureus* for 24 hours at 37° C. are reported in the tables.

EXAMPLES

Example 1

In order to determine whether an effective toxin-reducing amount of GML could be added to the absorbent structure while exhibiting low ether and water soluble substances and low foaming, GML was applied to Galaxy™ rayon fibers to result in mean 0.2% GML add-on to the fiber and the GML Galaxy™ rayon fibers were blended with standard non GML rayon fibers in the blends shown in Table 1. The fibrous structures were formed into compressed tampons with an apertured film cover (not treated with GML).

TABLE 1

| Sample | Blend Galaxy/GML | Blend Std. Rayon | GML on absorbent (wt-%) | Foam Pass/Fail | Water Soluble Substances (%) | Ether Soluble Substances (%) | Mean *S. aureus* Cfu Total | TSST-1 ug Total | Red. % |
|---|---|---|---|---|---|---|---|---|---|
| Control | 75% (no GML) | 25% | 0 | Pass | | | $6.9 \times 10e10$ | 269 | — |
| A | 75% (0.2 wt-% GML) | 25% | 0.15 | Fail | 0.63 | 0.15 | $7.0 \times 10e9$ | 4.8 | 98% |
| B | 50% (0.2 wt-% GML) | 50% | .01 | Fail | 0.77 | 0.11 | $1.20 \times 10e10$ | <0.5 | 99% |
| C | 10% (0.2 wt-% GML) | 90% | 0.02 | Pass | 0.47 | 0.07 | $2.9 \times 10e10$ | 9 | 97% |

In conclusion, it appears that Sample C is the only sample tested that showed an effective concentration of GML of 0.02% that can be obtained on the fiber blends tested to provide low foaming, low water extractables, low ether extractables, and significant reduction in TSST-1 formation. The fiber blend described is 10% of a 0.2% w/w GML rayon fiber blended with 90% non GML coated fiber to provide a total concentration of 0.02% GML on the tampon which is 5-fold less GML than that reported in U.S. Pat. Nos. 57,532, 522, 5,679,369, 5,705,182, 5,641,503, and 5,389,374.

Example 2

Since the preferred fiber concentration of GML is 0.02%, a study was set forth to determine whether GML could be loaded onto the cover alone in a concentration sufficient so as to be as effective as GML addition to the fiber. GML addition was evaluated on both plastic as well as nonplastic covers. Production of GML coating on nonwoven and film covers is described as follows:

Formulations:

GML in 50% PG (propylene glycol or 1,2-propanediol)/50% SPAN® 80 (sorbitan monooleate from Uniqema) or 50% PEG (polyethylene glycol)/50% SPAN® 80 vehicle.

The GML content in the formulation can be from 1-80% depending on the target GML add-on.

Tampons were produced with GML coated onto the cover (both Apertured Film and Nonwoven covers) of tampons and/or to blends of fiber in order to identify a concentration of an effective toxin-reducing amount of GML that exhibits low ether and water soluble substances and low foaming. In this experiment, tampons were exposed to *S. aureus* in a dialysis bag submerged into growth medium for 24 hrs. at 37° C. After incubation, the tampons were analyzed for *S. aureus* and TSST-1 concentration as described by Reiser et al. in the Journal of Clinical Microbiology, Vol. 25, August 1987, pp. 1450-1452.

The base film is a three layer co-extrusion constructed of polypropylene, polyethylene (LLDPE, LDPE, HDPE) and titanium dioxide as the whitening agent. The base film may also be produced as five layer co-extrusion ABCBA with layer A and B being the same and primarily polyethylene and C being polypropylene. The base film is then unwound and apertured via a vacuum/hot air process and then coated (50/50 PEG/SPAN) via a "Kiss Coating" system The coating that is placed on the film web will incorporate GML at a level to create a finish with about 0.1 to about 5 wt-% GML. A preferred level is between about 1 to about 3 wt-% GML add-on. The coating then goes through a chilling process to insure adherence to the film. The film is then wound and slit to required widths for processing into tampons.

Staple length viscose rayon fibers (available from Kelheim GmbH, Kelheim, Germany) were treated with various finishing compositions. The finish helps to make the fibers wettable and processable through manufacturing procedures. Standard rayon fibers were finished with an ethoxylated stearic acid finish. GML-treated rayon fibers were finished with GML to provide a 0.1 wt-% GML add-on to the fibers. The treated fibers were dried in preparation for blending, as described below.

GALAXY™ fibers (trilobal viscose rayon fibers, available from Kelheim GmbH) also were treated with various finishing compositions. Standard GALAXY™ fibers were finished with a a palmitic/stearic acid monester of polyethylene glycol. GML-treated GALAXY™ fibers were finished with GML to provide a 0.1 wt-% GML add-on to the fibers. The treated fibers were dried in preparation for blending, as described below.

Using carding equipment, various blends of the GML-treated and standard fibers were carded into fibrous webs. The carded webs were gathered into fiber rolls. The fibers were blended by hand and weighed to achieve the respective fiber

TABLE 2

Effect of GML addition to Apertured Film Cover on TSST-1 Production by *S. aureus*.

| Sample Description | GML Add-on to cover (wt-% of tampon) | GML Add-on to Fiber (wt-% of tampon) | *S. aureus* CFU Total × $10^8$ | TSST-1 Total ug | Reduction TSST-1 % |
|---|---|---|---|---|---|
| Tampon Control | 0 | 0 | 470 | 207 | — |
| Tampon Test 1 | 0 | 0.02% | 310 | 30 | 86% |
| Tampon Test 2 | 0.08% | 0 | 355 | 52 | 75% |
| Tampon Test 3 | 0.15% | 0 | 170 | 1.6 | 99% |
| Tampon Test 4 | 0.08% | 0.02% | 240 | <0.5 | >99% |
| Tampon Test 5 | 0.15% | 0.02% | 26 | <0.5 | >99% |

TABLE 3

Effect of GML Addition to Nonwoven Cover on TSST-1 Production by *S. aureus*.

| Sample Description | GML Add-on to cover (wt-% of tampon) | GML Add-on to Fiber (wt-% of tampon) | *S. aureus* CFU Total × $10^8$ | TSST-1 Total ug | Reduction TSST-1 % |
|---|---|---|---|---|---|
| Tampon Control | 0 | 0 | 150 | 30 | — |
| Tampon Test 1 | 0 | 0.02% | 15 | 9 | 70% |
| Tampon Test 2 9gsm cover | 0.05% | 0 | 5.8 | <0.5 | >99% |
| Tampon Test 3 9gsm cover | 0.05% | 0.02% | 5.0 | <0.5 | >99% |

The data reported above in Tables 2 and 3 show that toxin reduction can be achieved below the 0.1% add-on reported in U.S. Pat. No. 5,641,503. Further, the data suggest that the reductions in toxin achieved with GML addition to the fiber can be achieved by addition of GML to the cover alone.

Example 3

A series of experiments were conducted to determine whether the addition of

GML to different types of fiber affects the ability of GML to reduce TSST-1 concentration while not significantly impacting the viable *S.aureus*. In addition, the fibers are still able to pass the Foam Test.

Catamenial tampons comprising rayon fibers as their absorbent material were prepared as follows:

blends, wrapped with plastic apertured film (not treated with GML, unless otherwise noted, below), heat sealed, and inserted into an applicator for testing.

The tampons were tested in a microbiological laboratory. Tampons were inserted into sterile dialysis tubing and were inoculated with *S.aureus* Mn8 $1.2\times10^8$ cfu/ml. The entire assembly was submerged into nutrient agar and was placed into an incubator. After 18 hours of incubation at 37° C., the dialysis tubing was cut away from tampon was evaluated for TSST-1 level as well as the total viable *S.aureus* present within the tampon. The TSST-1 level was determined by Enzyme Linked ImmunoAssay while the total viable *S.aureus* count was determined using standard plate count as described by Reiser et al. in the Journal of Clinical Microbiology, Vol. 25, August 1987, pp. 1450-1452.

TABLE 4

Effect of GML Treated Rayon compared to untreated Galaxy on TSST-1 Production.

| Sample Description Treated Rayon/Untreated Galaxy | GML add-on to fiber (wt-% of tampon) | S. aureus cfu Total × $10^{10}$ | TSST-1 ug Total | % Reduction | Foam Test Pass/Fail |
|---|---|---|---|---|---|
| 0/100 | 0.0% | 2.4 | 115 | — | Pass |
| | | 2.6 | 137 | | |
| | | 2.6 | 118 | | |
| | | 2.7 | 98 | | |
| | | 2.7 | 108 | | |
| | | Mean = 2.6 | Mean = 122 | | |
| 10/90 | 0.01% | 2.5 | 121 | 2 | Pass |
| | | 2.5 | 109 | | |
| | | 2.6 | 82 | | |
| | | 2.6 | 145 | | |
| | | 2.6 | 137 | | |
| | | Mean = 2.6 | Mean = 119 | | |
| 25/75 | 0.025% | 2.6 | 117 | 0 | Pass |
| | | 2.5 | 146 | | |
| | | 2.6 | 99 | | |
| | | 2.5 | 132 | | |
| | | 2.6 | 117 | | |
| | | Mean = 2.6 | Mean = 122 | | |
| 50/50 | 0.05% | 2.0 | 73 | 50 | Pass |
| | | 2.1 | 69 | | |
| | | 2.3 | 82 | | |
| | | 2.1 | 46 | | |
| | | 2.0 | 37 | | |
| | | Mean = 2.1 | Mean = 61 | | |
| 75/25 | 0.075% | 2.0 | 46 | 55 | Pass |
| | | 1.9 | 53 | | |
| | | 2.1 | 62 | | |
| | | 2.0 | 48 | | |
| | | 1.9 | 66 | | |
| | | Mean = 2.0 | Mean = 55 | | |
| 90/10 | 0.09% | 2.0 | 15 | 91 | Fail |
| | | 1.9 | 13 | | |
| | | 2.0 | 11 | | |
| | | 2.1 | 9 | | |
| | | 2.1 | 9 | | |
| | | Mean = 2.0 | Mean = 11 | | |
| 100/0 | 0.1% | 2.1 | 10 | 88 | Fail |
| | | 2.0 | 14 | | |
| | | 2.1 | 17 | | |
| | | 2.1 | 13 | | |
| | | 2.1 | 18 | | |
| | | Mean = 2.1 | Mean = 14 | | |

The data in Table 4 show that 0.1% GML add-on level in a tampon containing only standard rayon fiber provides an 88% reduction in TSST-1 production, but it failed the foam test. Decreasing the GML add-on level to 0.075 wt-% decreased the foaming to permit the product to pass the foam test, but it was less effective in inhibiting the TSST-1 production.

TABLE 5

Effect of GML Treated Galaxy with Untreated Galaxy on TSST-1 Production.

| Sample Description Untreated Galaxy/GML Treated Galaxy | GML add-on to fiber (wt-% of tampon) | S. aureus cfu Total × $10^{10}$ | TSST-1 ug Total | % Reduction | Foam Test Pass/Fail |
|---|---|---|---|---|---|
| 100% Untreated | 0 | 2.4 | 151 | | Pass |
| | | 2.6 | 137 | | |
| | | 2.6 | 118 | | |
| | | 2.7 | 98 | | |
| | | 2.7 | 108 | | |
| | | Mean = 2.6 | Mean = 122 | | |
| 90/10 | 0.01 | 2.1 | 47 | 55% | Pass |
| | | 2.1 | 61 | | |
| | | 2.0 | 49 | | |
| | | 2.1 | 53 | | |
| | | 2.1 | 60 | | |

TABLE 5-continued

Effect of GML Treated Galaxy with Untreated Galaxy on TSST-1 Production.

| Sample Description Untreated Galaxy/GML Treated Galaxy | GML add-on to fiber (wt-% of tampon) | *S. aureus* cfu Total × $10^{10}$ | TSST-1 ug Total | % Reduction | Foam Test Pass/Fail |
|---|---|---|---|---|---|
| | | Mean = 2.1 | Mean = 54 | | |
| 75/25 | 0.025% | 2.0 | 73 | 50% | Pass |
| | | 2.1 | 69 | | |
| | | 2.3 | 82 | | |
| | | 2.1 | 46 | | |
| | | 2.0 | 37 | | |
| | | Mean = 2.1 | Mean = 61 | | |
| 50/50 | 0.05% | 2.1 | 44 | 72% | Pass |
| | | 2.2 | 39 | | |
| | | 2.0 | 26 | | |
| | | 2.1 | 31 | | |
| | | 2.0 | 32 | | |
| | | Mean = 2.1 | Mean = 34 | | |

In contrast to the data reported in Table 4, above, the data of Table 5 show that applying GML to Galaxy™ fibers (0.1 wt-% on the treated fibers) provides improved efficacy when blended with untreated Galaxy™ fibers. At 0.05 wt-% GML add-on in the fiber blend, the tampon passes the Foam Test and provides a 72% reduction in TSST-1 production without affecting the *S. aureus* viable cell number. The data in the above Table 5 show that for the lowest concentrations of GML tested of 0.01% showed measureable nominal 55% reduction in TSST-1 production while not significantly impacting the viable *S.aureus* concentrations. All the GML galaxy fiber concentrations tested passed the Foam Test. This suggests that the increased surface area of the trilobal rayon fiber provided by the Galaxy™ fibers allows for the GML concentration to be decreased while maintaining measurable TSST-1 inhibition at concentrations as low as 0.01 wt-% of the total fiber present.

TABLE 6

Untreated Rayon with treated GML Galaxy effect on TSST-1 Production.

| Sample Description Untreated Standard Rayon/GML Treated Galaxy | GML add-on to fiber (wt-% of tampon) | *S. aureus* cfu Total × $10^{10}$ | TSST-1 ug Total | % Reduction | Foam Test Pass/Fail |
|---|---|---|---|---|---|
| 100% Untreated Rayon | 0 | 1.9 | 185 | | Pass |
| | | 2.0 | 120 | | |
| | | 2.2 | 135 | | |
| | | 2.1 | 106 | | |
| | | 2.0 | 147 | | |
| | | Mean = 2.1 | Mean = 139 | | |
| 90/10 | 0.01 | 2.3 | 21 | 80% | Pass |
| | | 2.4 | 29 | | |
| | | 2.3 | 31 | | |
| | | 2.4 | 35 | | |
| | | 2.4 | 18 | | |
| | | Mean = 2.3 | Mean = 27 | | |
| 75/25 | 0.025% | 2.0 | 49 | 51% | Pass |
| | | 2.1 | 57 | | |
| | | 2.2 | 82 | | |
| | | 2.0 | 79 | | |
| | | 2.0 | 71 | | |
| | | Mean = 2.1 | Mean = 68 | | |
| 50/50 | 0.05% | 2.0 | 44 | 57% | Pass |
| | | 2.1 | 77 | | |
| | | 2.2 | 49 | | |
| | | 2.1 | 62 | | |
| | | 2.0 | 66 | | |
| | | Mean = 2.1 | Mean = 60 | | |

In Table 6 above, untreated standard rayon fiber was blended with 0.1% GML-treated Galaxy™ fiber to determine the impact of the 0.1% GML add-on of Galaxy™ fiber blended with untreated standard rayon fibers. Evaluation of tampons produced showed that again when GML-treated Galaxy™ fibers are utilized to make tampons, the tampons produced at low concentrations of 0.01')/0 GML to 0.05% GML reduced TSST-1 production from 51%-80% reduction while not adversely affecting the viable *S.aureus* population. Further, these tampon fiber blends passed the Foam Test at all three concentrations tested. Again, the data in Tables 5 and 6 show that when GML is applied to Galaxy™ trilobal fibers, lower add-on levels GML can be used on the fibers, and the resulting tampon structures can therefore pass the Foam Test. In addition, these tampons still provide reduced levels of TSST-1 production.

The specification, embodiments, and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent article comprising:

a) a fibrous absorbent structure;

b) a cover substantially enclosing the fibrous absorbent structure; and c) an active ingredient selected from the group consisting of:

i) monoesters of a polyhydric aliphatic alcohol and a fatty acid containing from eight to eighteen carbon atoms and wherein said monoester has at least one hydroxyl group associated with its aliphatic alcohol residue;

ii) diesters of a polyhydric aliphatic alcohol and a fatty acid containing from eight to eighteen carbon atoms and wherein said diester has at least one hydroxyl group associated with its aliphatic alcohol residue; and iii) mixtures of said monoesters and diesters; and wherein the fibrous absorbent structure:

A) has disposed thereon up to about 0.05 wt-% of the active ingredient

B) contains less than 0.3% ether soluble substances according to the Ether Soluble Substances Test, C) contains less than 0.7% water soluble substances according to the Water Soluble Substances Test; and D) passes the Foaming Test; and wherein the cover has disposed thereon up to about 5 wt-% of the active ingredient; and wherein the amount of active ingredient disposed on both the fibrous absorbent structure and the cover is sufficient to inhibit the production of toxic shock syndrome toxin-1 by Staphylococcus aureus bacteria when said product is exposed to said bacteria.

2. The absorbent article of claim 1, wherein the fibrous absorbent structure comprises multilimbed fibers.

3. The absorbent article of claim 2, wherein the multilimbed fibers are coated with active ingredient.

4. The absorbent article of claim 3, wherein the fibrous absorbent structure comprises less than about 75 wt-% of the active ingredient-coated multilimbed fibers.

5. The absorbent article of claim 1, wherein the active ingredient is present at less than about 0.02 wt-% of the fibrous absorbent structure.

* * * * *